United States Patent [19]
Choksi et al.

[11] 4,058,121
[45] Nov. 15, 1977

[54] VENTED NEEDLE FOR MEDICAL LIQUIDS

[75] Inventors: Pradip Vinobchandra Choksi, Northridge; Donald Leroy Johnston, Arcadia; Walter Seemayer, Burbank, all of Calif.

[73] Assignee: American Hospital Supply Corporation, Evanston, Ill.

[21] Appl. No.: 700,900

[22] Filed: June 29, 1976

[51] Int. Cl.$^2$ .............................................. A61M 5/00
[52] U.S. Cl. ................................ 128/221; 128/272.3
[58] Field of Search ............ 128/272.3, 272.1, 218 N, 128/218 R, 218 M, 221, 276

[56] References Cited

U.S. PATENT DOCUMENTS

| | | | |
|---|---|---|---|
| 2,746,455 | 5/1956 | Abel | 128/221 |
| 2,954,768 | 10/1960 | Hamilton | 128/221 |
| 2,989,053 | 6/1961 | Hamilton | 128/221 |
| 3,063,451 | 11/1962 | Kowalk | 128/221 |
| 3,757,780 | 9/1973 | Ishikawa | 128/218 N |

*Primary Examiner*—John D. Yasko
*Attorney, Agent, or Firm*—Larry N. Barger

[57] ABSTRACT

A thermoplastic needle for injecting sterile liquid into a vial with lateral turbulent motion while air from such vial escapes through a special vent groove on the needle. The needle also has spaced stop wings adjacent a rear portion of the vent groove to prevent overinsertion and occlusion of the vent groove.

13 Claims, 4 Drawing Figures

FIG. 1.
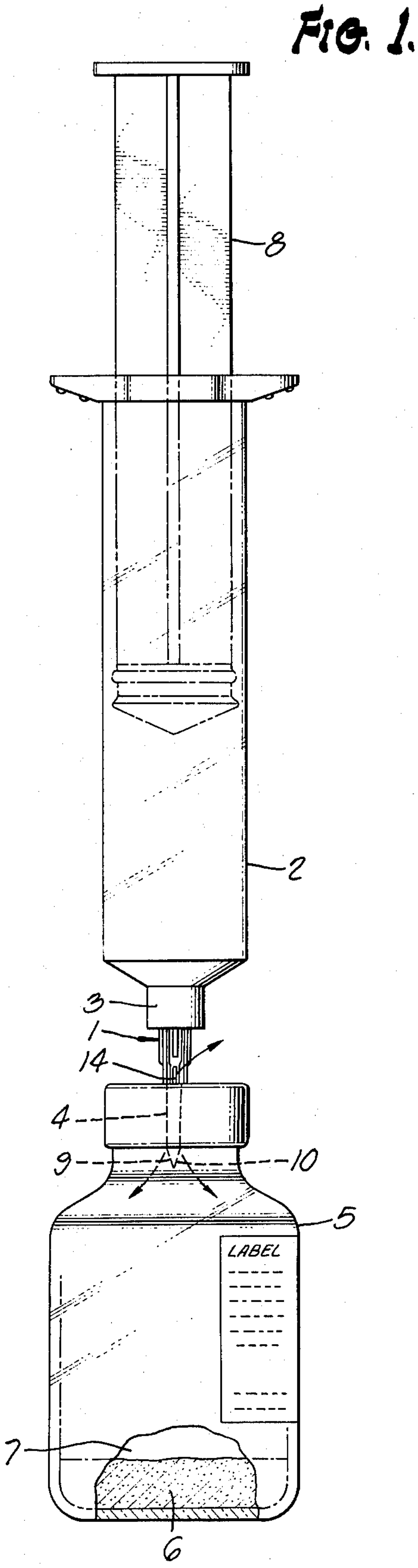
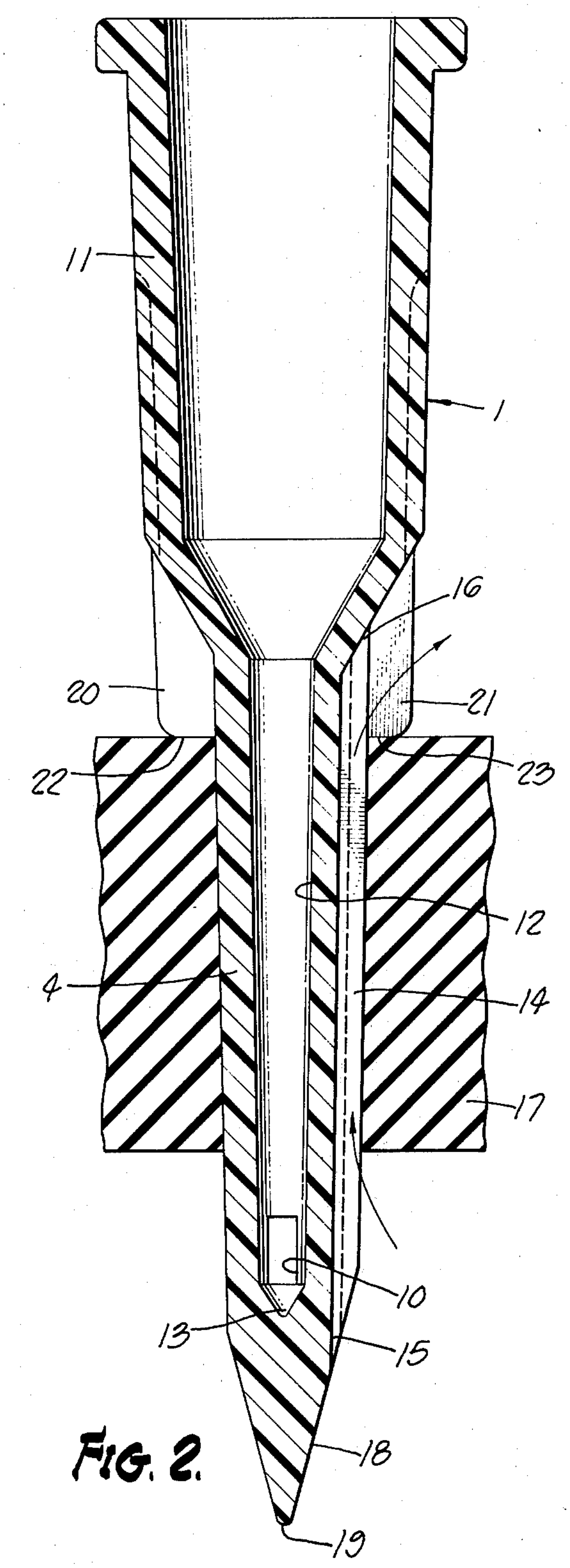
FIG. 2.

VENTED NEEDLE FOR MEDICAL LIQUIDS

BACKGROUND OF THE INVENTION

Many drugs are supplied to pharmacies in a dry or lyophilized form. These drugs are often supplied in rubber stoppered vials with a small portion of their internal volume containing the dry or lyophilized powder. Before such drugs can be used, the lyophilized powder must be dissolved in a sterile liquid. Aftr the lyophilized powder has been dissolved, it can then be extracted from the vial in small unit doses.

In the past, there has been a problem with quickly injecting the sterile dissolving liquid into the mixing vial. Small hypodermic needles with a sharpened beveled forward end, restricted liquid flow to a slow rate. Larger diameter double cut hypodermic needles sometimes cored the rubber stopper causing the needle to plug or a small rubber particle to fall into the vial. In addition, double cut hypodermic needles directed the liquid in a straight longitudinal stream causing its mixing force to be directed to only a small area near the center of the vial.

Also, with conventional metal hypodermic needles, there was a problem with pressure buildup. As liquid began to fill the vial, air within the vial was compressed. Upon removing the liquid filling syringe needle, the compressed air remained in the vial. Subsequently, when withdrawing small samples of the dissolved medicament from the vial, the operator had to be careful the pressure did not urge a plunger of a unit dose syringe rearwardly to inadvertently cause an overdose in the syringe.

SUMMARY OF THE INVENTION

We have overcome the above problems with a new thermoplastic vial filling needle that has one or more side delivery ports for turbulently injecting liquid into the container for rapid mixing with the dry powder. This improved needle has a closed forward end to substantially eliminate the coring problem, and a special air vent groove to prevent pressure buildup during liquid injection into the vial. The special needle also has a series of wing stop members near a rear of the vent groove to prevent overinsertion of the needle into the vial stopper to insure the vent groove is always exposed to the atmosphere.

BRIEF DESCRIPTION OF THE DRAWINGS

FIG. 1 is a front elevational view showing the needle connected to a filling syringe injecting liquid into a vial;

FIG. 2 is an enlarged sectional view of the needle of FIG. 1, without the attached syringe, and with only a portion of the vial stopper shown;

DETAILED DESCRIPTION

Figure 3:
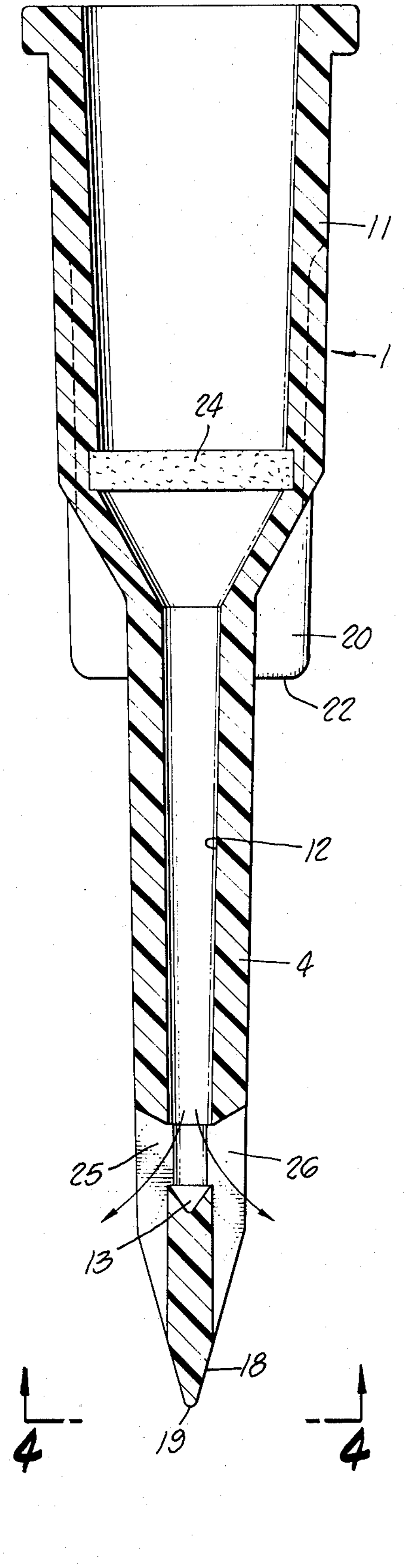
FIG. 3 is a second embodiment of the needle shown with a filter, and this sectional view as shown most readily at the lower end is taken at 90° to that section taken in FIG. 2.

In FIG. 1 the needle is shown generically as numeral 1 and is connected to a conventional hypodermic syringe 2. Syringe 2 has a Luer-lock collar 3 threadingly engaged with the needle 1. A cannula 4 of a needle (shown in dotted line) extends through a closure of vial 5. As shown in the broken away section at the bottom of FIG. 1, this vial contains a lyophilized powder drug 6, as well as a large portion of air 7. During the filling operation, shown in FIG. 1, a plunger 8 of syringe 2 is manually moved in a downward direction to turbulently spray liquid in a lateral direction from side ports 9 and 10 of cannula 4. The precise details of the special needle are better shown in the enlarged view of FIG. 2. Here the generic needle includes a cannula 4 and a hub 11. Hub 11 is designed to sealingly engage with the Luer-lock collar 3 and tapered Luer adapter (not shown) of syringe 2. As shown in FIG. 2 the cannula has a central passage 12 that extends to a forward end 13. Adjacent forward end 13 is lateral side port 10. Because of the 90° rotation from the view shown in FIG. 1, side port 10 appears to the rear of the viewer rather than to the right of the viewer. Along a right side of FIG. 2 is a vent groove 14 extending from a forward end 15 to a rearward end 16. The forward end 15 of groove 14 lies adjacent side port 10 so that a small protrusion of the needle's forward end beyond the inner surface of resilient rubber stopper 17 exposes the vial's interior to both a liquid discharge port and an air vent.

The forward end portion of cannula 4 is closed and has a generally conical forward tip 18 that terminates in a solid puncture point 19. This tip configuration substantially eliminates the coring problem with previous openended bevel cut hypodermic needles that were forced through rubber stoppers.

Near a juncture of the cannula 4 and hub 11 are a series of wings, two of which are shown at 20 and 21. These wings respectively have abutting surfaces 22 and 23 that engage an upper surface of the vial stopper. This limits the insertion distance of the needle, so a portion of the vent groove 14 adjacent its rear end 16 is always exposed to the atmosphere.

In the second embodiment of the invention shown in FIG. 3, the needle is identical to that shown in FIG. 2 with the exception of the optional filter 24 in the FIG. 3 embodiment. This filter 24 can act to strain out particulate matter from liquid within the syringe tube, and acts as an additional safety feature. The bottom end of the needle of FIG. 3 has this section taken at a 90° rotation from that section of FIG. 2. Hence, side ports 25 and 26 of the FIG. 3 embodiment correspond to the side ports 9 and 10 of the FIG. 1 embodiment. The arrows show the direction of lateral liquid flow from the two side ports.

Figure 4:
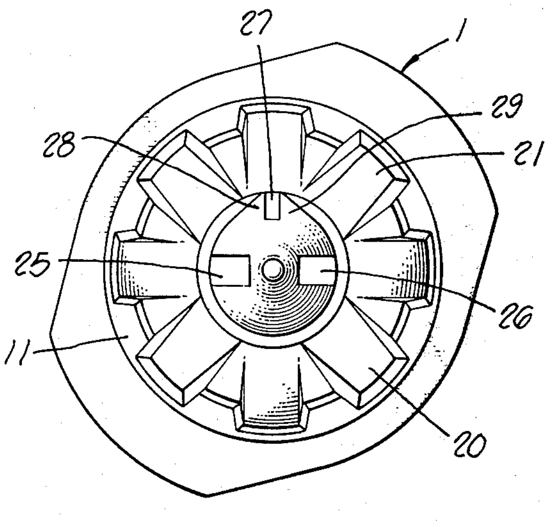
FIG. 4 is a bottom plan view of FIG. 3 taken along lines 4—4.

The relationship of the two side ports 25 and 26 and their relationship to vent groove 27 in the FIG. 3 embodiment is best shown in FIG. 4. The vent groove and side ports are circumferentially spaced 90° apart to prevent air from being sucked into the needle during drug aspiration. Bordering the edges of groove 27 are generally triangular segments 28 and 29 which extend longitudinally along the cannula. This gives the circumferential shape of the cannula a somewhat teardrop configuration. By use of the triangular segments 28 and 29, groove 27 does not interfere with the structural rigidity of the cannula. With this configuration, the cannula's external diameter is kept to a minimum to decrease drag when puncturing the vial's rubber stopper.

In the foregoing description the needle has been described as an implement for injecting liquid into a vial for mixing with dry lyophilized drugs. If desired, a separate sterilized needle of the same configuration shown in FIGS. 2 or 3 can be used to withdraw the liquid dissolved medicament from the vial. In such situation, the filter 24 of FIG. 3 would act to prevent particulate matter within the vial, from being sucked into the syringe. When the filtered needle to FIG. 3 is used to inject diluent into a vial as in FIG. 1, the needle also filters the diluent entering the vial.

The needle of this invention works very well when the cannula and hub are injection molded as a one-piece unit of transparent thermoplastic, such as polycarbonate. In this needle it has been found that a groove that is from 0.005 to 0.015 inch (0.127 to 0.381 millimeters) wide and is from 0.010 to 0.030 inch (0.254 to 0.762 millimeters) deep. The distance from the side port to the abutting surfaces 22, 23, of wings 20, 21 is preferably 0.300 to 0.500 inch (7.62 to 12.7 millimeters).

The needle as described above and with the dimensions specified work exceptionally well for rapidly injecting liquid into a vial without pressure buildup and without stopper coring. Although the needle can be used with an inverted (stopper downward) vial to extract liquid, it has been noted that occasionally some liquid seepage will pass through the air vent groove.

In the foregoing description, specific embodiments have been used to describe the invention. However, it is understood by those skilled in the art that certain modifications can be made to these embodiments without departing from the spirit and scope of the invention.

We claim:

1. A lateral delivery vented needle comprising: a cannula with a closed forward end, a rear end, and a side port adjacent its closed forward end; said cannula having a longitudinal external groove with a forward end adjacent the side port and with a rear end adjacent a rear portion of the cannula; stop means of the cannula preventing a rear portion of the groove from entering a container's resilient stopper; said cannula and stop means forming a unit that has a lateral gas vent means to an exterior of the stop means; and a hub joined to a rear portion of the cannula, whereby the needle can puncture a resilient closure of a container, and liquid can be laterally injected into the container through the cannula's side port, while gas within the container vents around the cannula's closed end to the cannula groove.

2. A vented needle as set forth in claim 1, wherein the groove is circumferentially offset from the side port about a circumference of the cannula.

3. A vented needle according to claim 1, wherein the cannula has two diametrically opposed side ports and the groove is spaced between these side ports.

4. A vented needle as set forth in claim 1, wherein the cannula has a tubular wall enclosing a longitudinal passage and the wall has a thickened portion containing said groove.

5. A vented needle according to claim 4, wherein the thickened section includes a generally triangular shaped segment bordering each edge of the groove.

6. A vented needle according to claim 1, wherein the needle has a filter secured to an interior of the needle.

7. A vented neeedle according to claim 1, wherein the stop means includes a plurality of lateral wings near a juncture of a cannula and hub, and a rear portion of the groove extends between two of these wings, and said wings have abutting surfaces that engage a container's resilient closure prior to insertion of the entire groove into such closure; and the lateral gas vent means is a lateral channel between said two wings.

8. A vented needle according to claim 7, wherein the distance between the wing's abutting surfaces and the side port is between 0.300 and 0.500 inch (7.620 millimeters to 12.700 millimeters) so the side port is located closely to an inner surface of a conventional rubber stopper of a vial when the stop means engage an outer surface of such stopper.

9. A vented needle according to claim 1, wherein the cannula's closed forward end is generally conical for puncturing.

10. A vented needle according to claim 1, wherein the hub and cannula are an integral one-piece thermoplastic unit.

11. A vented needle according to claim 1, wherein the groove extends longitudinally along the cannula and has a width of from 0.005 to 0.015 inch (0.127 to 0.381 millimeters) and a depth of from 0.010 to 0.030 inch (0.254 to 0.762 millimeters).

12. A vented needle with an externally longitudinally grooved cannula having a forward end and a rearward end and a hub connected to a rearward portion of the cannula, wherein the improvement comprises: a stop means on the needle for engaging a container closure prior to complete insertion of the groove into such container closure; said stop means and cannula forming a unit that has a lateral gas vent means to an exterior of the stop means, thereby insuring that the groove is always exposed to the atmosphere.

13. A vented needle according to claim 12, wherein the stop means includes a plurality of wings with abutting surfaces for engaging a container closure, and the groove is positioned between two wings and extends rearwardly beyond the abutting surfaces of such wings; and the lateral vent means is a lateral channel between the two wings.

* * * * *